(12) United States Patent
Hruschka et al.

(10) Patent No.: US 10,160,776 B2
(45) Date of Patent: Dec. 25, 2018

(54) METHOD FOR ACQUIRING ONE OR A PLURALITY OF RECYCLABLE MATERIALS FROM SEEDS

(71) Applicant: GEA MECHANICAL EQUIPMENT GMBH, Oelde (DE)

(72) Inventors: Steffen Hruschka, Oelde (DE); Detlef Ullmann, Oelde (DE); Wladislawa Boszulak, Oelde (DE)

(73) Assignee: GEA MECHANICAL EQUIPMENT GMBH, Oelde (DE)

(*) Notice: Subject to any disclaimer, the term of this patent is extended or adjusted under 35 U.S.C. 154(b) by 118 days.

(21) Appl. No.: 15/302,586

(22) PCT Filed: Mar. 25, 2015

(86) PCT No.: PCT/EP2015/056429
§ 371 (c)(1),
(2) Date: Oct. 7, 2016

(87) PCT Pub. No.: WO2015/155010
PCT Pub. Date: Oct. 15, 2015

(65) Prior Publication Data
US 2017/0029449 A1 Feb. 2, 2017

(30) Foreign Application Priority Data

Apr. 8, 2014 (DE) .................. 10 2014 104 986

(51) Int. Cl.
*C07F 9/10* (2006.01)
*C07F 9/117* (2006.01)
(52) U.S. Cl.
CPC .............. *C07F 9/117* (2013.01); *C07F 9/106* (2013.01)
(58) Field of Classification Search
CPC .................................. C07F 9/106; C07F 9/117
See application file for complete search history.

(56) References Cited

U.S. PATENT DOCUMENTS

| | | | |
|---|---|---|---|
| 4,668,813 | A | 5/1987 | Ogawa et al. |
| 5,574,180 | A | 11/1996 | McQuigg et al. |
| 2005/0136162 | A1 | 6/2005 | Kvist et al. |
| 2015/0327572 | A1 | 11/2015 | Hruschka et al. |

FOREIGN PATENT DOCUMENTS

| | | |
|---|---|---|
| DE | 69223315 T2 | 3/1998 |
| DE | 102011050905 A1 | 12/2012 |
| DE | 102011105914 A1 | 1/2013 |
| DE | 102013114698 A1 | 7/2014 |
| EP | 1145642 A1 | 10/2001 |
| EP | 1272048 B1 | 5/2008 |
| WO | 2013001043 A2 | 1/2013 |
| WO | 2014102176 A1 | 7/2014 |

OTHER PUBLICATIONS

German Search Report created on Dec. 11, 2014 in related DE Application No. 10 2014 104 986.1.
International Search Report dated Jun. 17, 2015 in related International Application No. PCT/EP2015/056429.
Written Opinion dated Jun. 17, 2015 in related International Application No. PCT/EP2015/056429.
Office Action dated Feb. 12, 2018 in related EP Application No. 15 713 855.3.

*Primary Examiner* — Joseph R Kosack
(74) *Attorney, Agent, or Firm* — Patent Portfolio Builders PLLC

(57) ABSTRACT

A method for acquiring at least one or a plurality of recyclable materials, in particular phytic acid, from a native material quantity containing phytic acid or phytate is provided. The method involves providing a native, reduced material quantity containing phytic acid and/or phytate made from seeds containing phytic acid. The reduced material quantity is pre-treated in order to obtain a flowable alkaline, preferably alcoholic-alkaline mash. A solid phase, which has phytic acid and/or at least one phytate, is separated from the mash. Phytic acid and/or at least one phytate is isolated from the solid phase.

11 Claims, 2 Drawing Sheets

METHOD FOR ACQUIRING ONE OR A PLURALITY OF RECYCLABLE MATERIALS FROM SEEDS

BACKGROUND AND SUMMARY OF THE INVENTION

Figure 1:
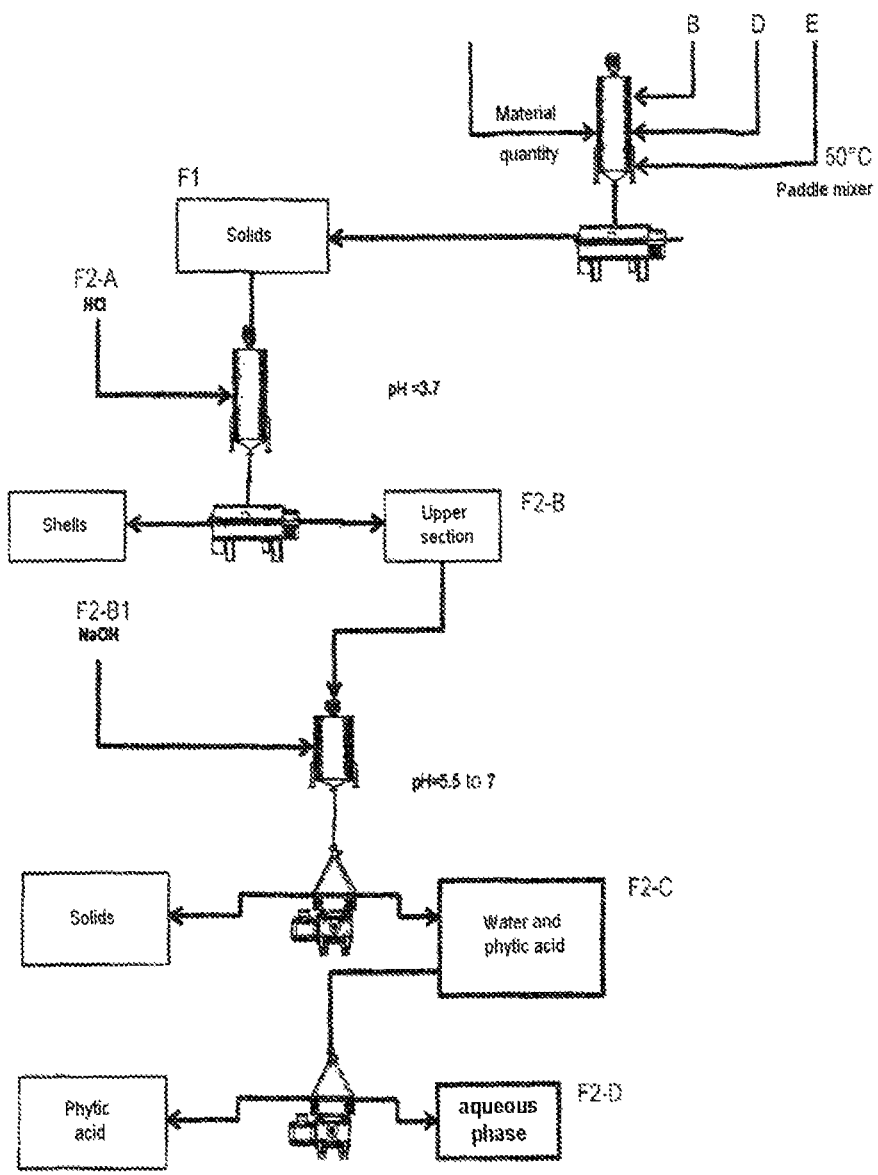

Exemplary embodiments of the invention relate to a method for acquiring at least one or a plurality of recyclable materials from a native material quantity containing phytic acid.

Acquiring (extracting) a protein phase as a recyclable material phase from seeds with hard, breakable shells, in particular from rape fruits, is known to the prior art. In particular the method of German patent document DE 10 2011 050 905 A1 makes it possible to acquire highly pure proteins, as among other things by increasing the solubility of the proteins, bonds to pollutants consisting of, for example, cellulose, shells, and the like are evidently also loosened. Many seeds used for this purpose contain phytic acid. Among other things, phytic acid supports growth in plants, but it is not necessarily desirable in the protein phase. If the material quantity or the seed used for protein extraction contains phytic acid, then it is of value to separate this material or rather the corresponding phytic acid, possibly also as phytate, from the protein and to extract it either alone or in addition to a protein phase as a recyclable material phase.

Given this background, the problem addressed by the invention is that of providing a method for extracting a phytic product, in particular phytic acid or phytate, from a native material quantity containing phytic acid, and perhaps also for extracting additional recyclable materials such as the aforementioned protein phase.

BRIEF DESCRIPTION OF THE DRAWING FIGURES

Figure 2:
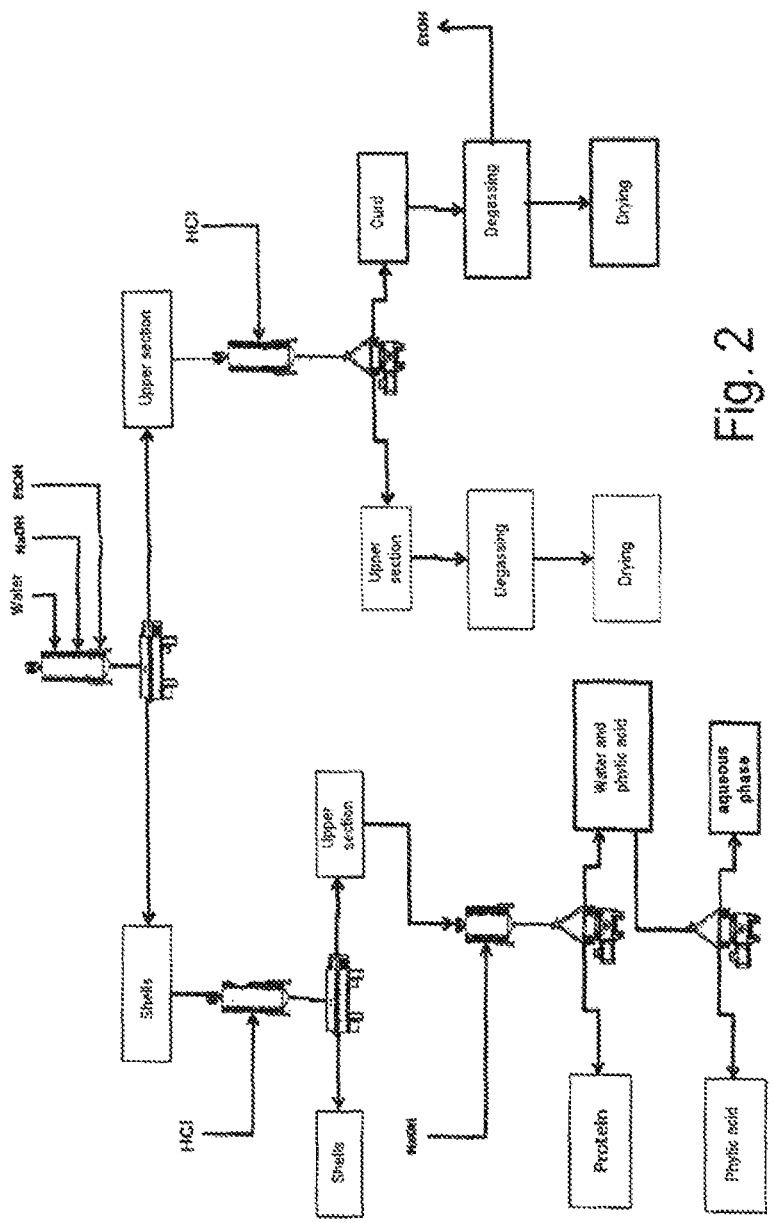

FIGS. 1 and 2 are block diagrams illustrating exemplary methods in accordance with the present invention.

DETAILED DESCRIPTION

According to an aspect of the invention, a method of the invention for extracting at least one or a plurality of recyclable materials from native material quantities containing phytic acid, wherein the at least one recyclable material is a phytic acid product, in particular phytic acid and/or a phytate has the following steps:

Step A: Supplying a native material quantity containing phytic acid from seeds containing phytic acid with hard, breakable shells, in particular from rape fruits, in particular as a material quantity from the whole seeds or from already (partially) de-oiled seeds, in particular as press cake left over as residue from an oil extraction process, in particular with a press, or as expeller meal left over as residue from a hexane extraction process.

Step B: If the material quantity from step A has not already been comminuted: comminuting the material quantity, wherein the shells are broken open at any rate.

Step C: Dispersing the comminuted material quantity from step A) or B) with water or with an aqueous solution, wherein preferably up to 8 parts maximum, particularly up to 6 parts maximum, in particular up to 5 parts maximum of water are added to one part of comminuted material quantity and wherein the water and the comminuted material quantity are stirred in order to obtain a flowable mash or dispersion;

Step D): Adjusting the pH value of the mash (I) from step C) in an alkaline range of pH>9.5;

Step E): Adding a water-soluble organic solvent, in particular a water-soluble alcohol, in particular ethanol, to the mash D), in particular following the adjustment of the pH value of the mash in step D), in particular in such a way that an alcohol concentration of less than 30 vol. % is reached in order to detach the shells from the endosperm of the seeds/fruits;

Step F1): Separating a solid phase, which has the predominant fraction of the shells, from the mash from step E), preferably in a centrifuge in the centrifugal field;

Step 2F): Isolating phytic acid or phytates from the solid phase of step F).

Chiefly phytic acid and the acquisition (extraction) thereof shall be described in the following. However, it is understood that the salts of phytic acid, or phytates, are also extractable or perhaps present in dissolved form. Phytic acid or a phytate may be present, depending upon the pH.

The method described above should be understood as not being limited with respect to the sequence of steps B), C), and D). Steps B), C), and D) can also be carried out simultaneously or in transposed sequence. However, preference is given to the chronological order of B), then C), and then D).

As source material, the native material quantity is supplied from seeds with hard, breakable shells, in particular from whole seeds/fruits of crucifers (*Brassicaceae*), in particular from rape fruits. After step A), the shell fraction in a particularly preferred embodiment can still contain 100% of the shell fraction of the unshelled seed. However, the processing of seed with a lower shell fraction is also conceivable.

According to the invention, contrary to expectations it was shown that the preprocessing of steps C), D), and E) results in the phytates or phytic acid of the seed being in the recoverable form of a solid phase containing the shells. After the separation of the shell fraction from the solid phase according to step F1), it is thus possible to extract the phytic acid as a recyclable material either directly from the solid phase with the phytic acid and the shell fraction or after additional method steps have been carried out—the latter being particularly advantageous.

According to a particularly advantageous variant of this method, to this end step F2) has the following sub-steps:

Step F2-A): Mixing the solid phase from step F1) with water and/or with an aqueous solution, in particular with diluted hydrochloric acid, so as to give rise to a flowable, shell-containing, and water-saturated phase containing phytic acid and/or phytates whose pH value is shifted into an acidic pH range, preferably pH<4; and Step F2-B): Separating a solid phase, which has the predominant fraction of the shells, from a liquid phase containing phytic acid and/or phytates, and F2-C): Separating the phytic acid from the liquid phase containing phytic acid or phytates.

Mixing the solid phase from step F1) with water or with an aqueous solution and shifting the pH value into the acidic range, in particular to a value of pH≤5.1, gives rise in an expedient manner to a solid/liquid mixture whose liquid phase at any rate contains a substantial fraction of the phytic acid that was contained in the seed used as a source material.

The following additional sub-step in between steps F2-B) and F2-C) for extracting the phytic acid is then advantageous:

Step F2-61): Shifting of the pH of the liquid from step F2-61) into a less acidic range, preferably with a pH value of pH>5.

The phytic acid can thus be extracted in an expedient manner as a phytic acid product and (optionally after the separation of step F2) isolated in relatively pure form.

Overall this gives rise in an expedient manner to the possibility of extracting phytic acid from the seed containing phytic acid or from the intermediate product containing phytic acid produced from the seed.

The invention furthermore creates the general method for the extraction of at least one or a plurality of recyclable materials, in particular of a product, preferably of phytic acid or phytate, from a native material quantity containing phytic acid, with the following steps:

100) Supplying a comminuted native material quantity containing phytic acid and/or phytate from seed containing phytic acid and/or from intermediate seed products containing phytate, 200) Pretreating the comminuted material quantity in order to obtain a flowable alkaline, preferably alcoholic-alkaline mash;

300) Separating a solid phase that contains phytic acid and/or at least one phytate from the flowable mash, preferably in a centrifuge in the centrifugal field; and 400) Isolating phytic acid and/or of at least one phytate from the solid phase after additional steps have been carried out.

Again it is particularly advantageous if the comminuted phytic acid-containing native material quantity consists of phytic acid-containing seeds with all of the shells or a portion (in particular more than 30%, preferably more than 50%) of the shells of the seeds and if during the pretreatment step the phytic acid is shifted into a shell-containing solid fraction of the material quantity. However, the processing of a material quantity without a shell fraction is also possible. Hence it is also expedient if the comminuted native as well as phytic acid-containing and/or phytate-containing material quantity consists of phytic acid-containing seeds without their shells and if the phytic acid and/or at least one phytate is initially shifted into a solid fraction of the material quantity.

In order to extract the phytic acid, it is advantageous if step 400) has the following sub-steps:

Step 400-A): Mixing the solid phase from step 300) with water and/or with an aqueous solution, in particular with diluted hydrochloric acid, so as to give rise to a flowable, shell-containing, and water-saturated phytic acid-containing and/or phytate-containing phase whose pH value is shifted into an acidic pH range; and Step 400-B): Separating a solid phase, which optionally has the predominant fraction of the shells, from a phytic acid-containing and/or phytate-containing liquid phase and F400-C): Separating the phytic acid from the phytic acid-containing or phytate-containing liquid phase directly or after carrying out one or a plurality of additional steps.

In doing so, further preference is given to carrying out the following sub-step between steps F400-B and F400-C:

F400-61): Shifting of the pH value of the liquid phase from step F400-B) into a range with a pH value of pH>5.

Exemplary embodiments of the invention also relate to a phytic acid product, preferably phytic acid or phytate, produced from a native material quantity containing phytic acid or phytate according to a method described above.

The pretreatment step in this process preferably comprises steps C) through E). Again the steps of separating and extracting the phytic acid can have a plurality of additional sub-steps, as described in the preceding.

The following should also be noted regarding steps A) through F1).

Step A:

The material quantity in the sense of this patent application can consist of the whole but crushed seeds.

But as an alternative, the material quantity can also consist of an already de-oiled product, in particular an "intermediate product", namely a press cake left over as oil extraction residue after a "preliminary step" such as the extraction of oil, in particular with a press (e.g., a screw press).

Particular preference is given to processing "intermediate product recently obtained beforehand" as the source material, in other words no more than 31 days may have passed since the preliminary step.

While the seed can be freshly harvested or it can be several days, weeks, or months old, the intermediate step (the pressing) should take place shortly or even immediately before the further processing so that the material, i.e., the seed, will not have changed too much after the oil extraction.

Definite preference is given to processing "fresh material" as the source material, in other words no more than 3 days, preferably even less than 48 hours or 24 hours or 12 hours or less than 1 hour, may have passed since a preliminary step or preliminary processing (oil extraction).

In terms of the yield and purity of the recyclable products, good results are obtained with material from a time period shortly after the preliminary step, and as a rule even better results are obtained with fresh material.

The press cake can also have a residual oil content of 20 vol. % or more. Despite such high residual oil contents, the extraction of a protein phase is also achievable in an expedient manner with the invention.

Step B:

If it is still not in comminuted form: comminuting the material quantity from step a) to break open the shells. If a press cake is used, the latter is broken up while still warm, ideally immediately after the pressing. A comminuted material, specifically a type of granular material, is thus produced from the press cake. As a rule the material quantity (partially) de-oiled beforehand by a pressing process is just comminuted, for example ground, or at any rate the shells are broken open.

Step C:

The material quantity obtained and comminuted from step A) or B) is dispersed with water. Preferably up to 8 parts maximum, preferably up to 5 parts maximum of water are added to one part of "comminuted product". The water and comminuted product are then stirred so as to obtain a flowable mash or dispersion. The stirring is preferably done for 15 minutes or longer, also longer than 30 minutes, in particular longer than 1 hour. An aqueous solution can also be used as an alternative or in addition to water. This solution can contain other dissolved organic or inorganic constituents (e.g., salts or water-soluble organic solvents).

Step D)

Next the pH of the mash (I) from step C) is adjusted in an alkaline range; the pH of the mash or dispersion is preferably adjusted to 10 to 11 with an alkaline solution. In doing so the stirring is continued (with caution). The stirring time is 15 minutes or longer, preferably longer than 30 minutes, and is preferably 1 hour or longer.

Step E)

In this additional step, at least one water-soluble organic solvent is added to the mash after the adjustment of the pH thereof in step D. The dispersion whose pH value has been adjusted in the alkaline range is preferably brought to an alcohol concentration of 15-20 vol. % or less, in particular 12 vol. %, with the alcohol ethanol (preferably 30-60% ethanol). The amount of water in step C can be reduced by an amount corresponding to the amount of water in the alcohol used, particularly in the 30-60% ethanol. The shells thus detach from the cotyledon with the residual oil and can be separated out, in particular centrifugally.

Steps C-E are preferably carried out in succession, but as an alternative they can also be carried out jointly, that is simultaneously. The sequence is less decisive for the extraction of phytic acid. This simultaneous addition is achievable by adding, for example, diluted ethanol solution in which NaOH is present in dissolved form. In this case, the addition of an alcohol, of water or of an aqueous solution as well as the shifting to an alkaline pH by adding the above-mentioned mixture take place as a combination of steps C-E.

Step F1)

In step F), a solid phase comprising the predominant fraction of the shells is separated from the mash, preferably in a centrifuge in the centrifugal field, or the mash is cleared of shell-solid fractions by settling, particularly in a decanter.

In the following, at times the term "upper section" will be used to refer to the lighter phase of a centrifugal phase separation, and the solid phase shall be referred to as the heavy phase. Accordingly, in terms of its density a middle phase would lie in between these two.

A particular advantage of the method of the invention lies in the fact that after step F), additional recyclable materials can be extracted from the phases separated in that step. This shall become clear from the description further below.

An additional recyclable phase can be extracted from the upper section (that is, from the liquid phase).

To this end, the following additional steps are carried out after step F1):

Step G)

The mash of the upper section from step F1), which is at any rate as shell-free as possible, is likewise further processed. In this further processing, the dissolved protein fraction is preferably precipitated out of the shell-free mash, which together with the undissolved or dissolved protein portion forms a fraction known as curd. In this process the pH value is again shifted further into the acidic range, in particular into the pH=4.5 to pH=7 range.

Step H)

The shell-free mash of the upper section whose pH value has again been shifted into the acidic range is then separated (preferably in a centrifuge, particularly in at least one decanter or in a separator) in one or two steps into recyclable material phases, one of which phase is a concentrated protein phase.

Particular preference is given to a separation into the following two or three phases:

oil-containing phase aqueous phase (containing polyphenols, carbohydrates, and sinapinic acid);

protein concentrate phase (aka "protein curd" in the following), or aqueous phase with albumin content and residual oil content; and protein concentrate phase (protein curd).

The two-phase separation is chosen if the raw material has been relatively substantially de-oiled and/or is bound in the solid material or if the liquid phase was not subjected to intense shearing in step 1. Water or alcohol or alkaline solution or the like can also be added in sub-steps. As the lighter phase, the oil contains triglycerides and is one of the extractable recyclable materials.

The temperature during all method steps is preferably below 60° C., in particular below 50° C., preferably between 40° C. and 50° C., whereby it is possible to extract particularly valuable, in some cases temperature-sensitive products in a gentle manner.

The denaturing of proteins is a temperature- and time-dependent process. Plus there is the alcoholic medium requirement. The higher the temperature, the faster protein denaturing takes place. In an aqueous environment, irreversible protein denaturing is not to be expected under the influence of heat at temperatures of 45-50° C. However, this changes with the alcohol concentration. With highly concentrated alcohol, protein precipitation is observed even at ambient temperature. The lower the alcohol concentration, the higher the temperature has to be in order to denature the proteins. Or conversely: the more dilute the alcohol concentration is, the higher the process temperature may be without the proteins being irreversibly damaged.

Thus, a temperature as high as possible, in other words as close as possible to 60° C., will be selected (for pure water) in order to dissolve as many materials as possible, such as proteins, lecithins, glycolipids, etc. Cellulose, lignin, and materials such as sodium or Ca phytates can thus be separated out as difficult to dissolve or insoluble constituents of the shell fraction or with the shell fraction. However, care must be taken to ensure that the temperature remains sufficiently low in accordance with the process parameters time and alcohol concentration (and perhaps pressure).

The precipitated proteins are present as protein curd (heavy phase). They constitute another of the extractable recyclable materials. This phase can be readily dried to a powder.

Overall, a protein concentrate phase is acquired that also has visual appeal and is therefore well-suited for recycling, which can be assigned the values RAL 1015 (light ivory) or RAL 1013 (pearl white), or classified as a blend of these two tones, in an RAL color classification scale. Standardized colors are designated as RAL colors (RAL GmbH, subsidiary of the RAL Institute). A four digit color number is assigned to each color. Theoretically, any press cake can be used for the method.

The advantageous temperature specification for method steps A) through H) does not apply to the press temperature during the production of the press cake during the oil extraction. The higher the temperature was during the preceding process steps, the browner the protein phase or curd fraction becomes. This is due to the Maillard reaction of sugars with proteins on the one hand, and to phenol oxidation on the other hand. Compared to German patent document DE 10 2011 050 905 A1, a particularly appealing product especially well-suited for recycling is obtained, in particular due to the use of optimally selected source material (preferably cold-pressed rape press cake, preferably very fresh).

The use of cold-pressed material, in particular a cold-pressed rape press cake (temperature during the pressing process advantageously less than 70° C., particularly preferably even less than 60° C.) as source material or as the supplied material quantity is particularly advantageous. During the pressing process, hot-pressed material is exposed to considerably higher temperatures (up to 100° C. and above). By using cold-pressed material as source material for the method of the invention, it is possible to obtain a protein phase or protein and/or curd phase with considerably better properties (considerably lighter in terms of color and thus better suited for processing, with a considerably higher water binding capacity of, for example, 1 part curd powder+3 parts water) and with a considerably better yield than by using warm- or hot-pressed source material. Until now this was unknown in the prior art. The aim of standard rape pressing techniques is a high oil yield, which is why preference is given to using higher temperatures during the pressing process. As a side effect, it must be stated that polyphenol is degraded, which per se would be advantageous for the protein fraction. However, the original (i.e., non-reduced) polyphenol content in the cold-pressed cake does not pose any problem for the final product with the method of the invention because the polyphenol compounds are transferred to the aqueous phase and are therefore essentially not present in the curd phase.

Hence the curd phase (which according to the inventive method was extracted from a press cake that was additionally de-oiled with hexane beforehand) is more appropriately assigned to the RAL tone 1024 ochre or to 1014 ivory. Preference is given to the processing taking place under ambient pressure.

Additional valuable ingredients are also contained in the aqueous phase, which is relatively rich in albumin. Building up the albumin concentration, for example by filtering the aqueous phase from the preceding step, in order to obtain the albumin phase as another recyclable material is therefore practical and advantageous.

A particularly advantageous method variant will be explained with reference to the following example.

Steps A, B): In this example, the source material is rape press cake (or also sunflower meal or legume flour, ideally supplied by gentle cold pressing and with typical residual oil contents of 10%, although even higher oil contents will not pose any problems). The cake is broken up, ideally immediately after pressing while still warm.

Step C): The cake granular is dispersed in water (1 part cake and 6 parts water maximum) and stirred carefully (for 1 hour).

Step D): After or during step B), the pH of this dispersion is adjusted with an alkaline solution, preferably a NaOH alkaline solution, to 10 to 11 and stirred carefully, preferably for 15 minutes to 1 hour.

Step E) The dispersion from step D) is brought to a 12% EtOH concentration with EtOH (ethanol, preferably 30-60% ethanol); the amount of water is thus reduced by the amount of water contained in this 30-60% EtOH.

Step F1) In the ethanol, the shells detach from the endosperm (cotyledon) with the residual oil and can be separated, for example by centrifuging, with the phytic acid, which surprisingly collects on the shell fraction or rather the solid phase containing the shells as part of the solid phase.

Carrying out the method with other water-soluble organic solvents such as other water-soluble alcohols, for example isopropanol, is also conceivable.

Calcium hydroxide can also be used in the method. This generates Ca phytate, which is less soluble than a Na phytate. In this final pH shift from the acidic to the less acidic range to the neutral range, the dissolved phytic acid precipitates out as phytate and can thus be separated from the fluid, for example by centrifuging, gravitation, or filtration.

Experiment 1:

A shell fraction containing phytic acid and extracted with steps A) through F1) as described above was further processed in order to extract phytic acid.

To this end, 220 g of the shell fraction were mixed with 300 g of water at room temperature (in this case 20° C.) in step F2-A). The reaction time was 5 minutes. After 5 minutes, the pH value of the shell/water mixture was shifted into the acidic range to a pH=3.7 using hydrochloric acid (in this case 11.1 g of 10% hydrochloric acid (HCl)) (step F2-B). The reaction time was 5 minutes.

A spin test showed that a shell phase making up ca. 30% of the volume of the sample settled out on the very bottom of the beaker. Above this lay a yellow protein phase making up ca. 15% of the volume, above which a cloudy, yellowish water-alcohol-phytic acid phase making up 54% of the volume had collected. Lastly, a supernatant layer that could not be clearly identified and that made up ca. 1% of the volume in the beaker had collected over this water-alcohol-phytic acid phase (step F2-C1).

On the industrial scale, the solid phase can be allowed to settle out of the water-alcohol-phytic acid phase, or it can be separated therefrom in another manner, for example centrifugally, particularly in the decanter.

It is then advantageous if the pH value of the liquid phase from step F2-C1 is shifted into a less acidic, preferably neutral range. In the experiment, this was done by adding 0.87 g of 16% sodium hydroxide solution to the yellow water-alcohol-phytic acid phase. In the spin test, phytic acid collected at the bottom of the beaker and made up ca. 5% (vol. %) of the liquid phase, above which a water/alcohol phase had settled, which made up ca. 94% of the liquid phase. A supernatant layer that could not be clearly identified and that made up ca. 1% of the volume in the beaker formed above this water/alcohol phase (step F2-C1).

A total of a few grams of phytic acid can be extracted in this manner from the shell fraction from step F1).

The phytic acid content in the rape press cake is typically 3-4 wt % of the dry mass of the rape press cake. It increases to ca. 6-7 wt %, for example, of the dry mass of the rape press cake if shelled seeds are used. With the use of seeds in the rape press cake that still contain part of their original shells (e.g., 30% or more of the shells), the shell-specific phytic acid content increases accordingly.

Experiment 2:

A shell fraction containing phytic acid and extracted with steps A) through F1) as described in the preceding was further processed in order to extract phytic acid.

To this end, 100 g of the rape shell fraction were mixed with 150 g of water at room temperature (in this case 20° C.) in step F2-A). The reaction time was 5 minutes. After 5 minutes, the pH value of the shell/water mixture was shifted into the acidic range to a pH=3.7 using hydrochloric acid (in this case 3.4 g of 10% hydrochloric acid (HCl)) (step F2-B). Again the reaction time was 5 minutes.

A spin test showed that a shell phase making up ca. 30% of the volume of the sample had settled out on the very bottom of the beaker. Above this lay a yellow protein phase making up ca. 20% of the volume, above which a somewhat darker phytic acid phase making up 3% of the volume had collected. A water/alcohol phase making up ca. 47 vol. % had collected above this phytic acid phase. The phytic acid phase can in turn be separated separately.

Additionally, at any rate it is possible to extract a protein phase from the liquid phase from step F1) in each case.

To this end, it is expedient to precipitate the protein from the upper section by acidifying the light phase, preferably to a pH=4.5 to 7.2. After the separation, prior to acidification this light phase initially has a pH value of preferably 9.7 to 10.5.

The separation into an oil-aqueous phase-protein concentrate phase (protein curd) or the separation into an oil/water phase and protein concentrate phase can be supported by an intense shearing in order to expedite the release of the oil.

Preference is then given to a separation of the precipitated protein as curd taking place in the heavy phase, which as a rule is the solid phase or the so-called curd phase. Additionally, triglycerides can optionally be extracted as light oil from the upper section, i.e., the light phase, in particular by centrifuging and perhaps by filtering the water phase to build up the albumin concentration.

The wet separation of the shells from the detached and swollen proteins with simultaneous displacement extraction of the triglycerides (oil phase) from the oil- or residual oil-containing press cake or legume flour and simultaneous phenol extraction should be mentioned as particularly advantageous.

The particular advantages of the method are:

With the method described in the preceding, low dilutions and thus low volume flows in the process are achievable with little solvent waste.

A higher polyphenol concentration during the extraction in the aqueous phase results (method steps 2 through 5).

Because the process is carried out at maximum temperatures of 50-55° C. or lower, native temperature-sensitive proteins are also contained in the final product.

Overall, comparatively high protein yields of up to 70% are achievable, wherein up to 45% and ca. 22-24% can be extracted from the "curd phase" and from the albumin phase, respectively.

Because shell residue as well as polyphenols, carbohydrates, phytic acid and/or phytates, lignin, and cellulose are completely removed or depleted, a higher quality final product (protein mixture) can be obtained.

The protein phase contains "native" protein whose swellable fraction remains swellable after the extraction and whose water-soluble fractions remain water soluble after the extraction. The protein phase is furthermore nearly triglyceride-free and has only low residual oil values, mainly polar lipids.

The good medium for microorganism growth due to the low alcohol concentration simplifies the process hygiene.

Diluted, the alcohol can be re-used in the cycle.

In this case, a wet separation of the shells initially takes place rather than the extraction of undesired materials from the highly de-oiled, ultra-finely comminuted source material rape meal or rape cake that is typical of the standard methods. This is accomplished in a multi-step process by the cake being broken up first without comminuting the kernel fragments any further.

It is particularly advantageous to leave the shells as large as possible. They should preferably have a mean diameter of 0.5 mm or more. Oil droplets do not need to be larger; "particles" rather than individual molecules or small molecule clusters are important.

Water is then added, with careful stirring in the alkaline range. The water-soluble portion of the proteins is thus dissolved while another portion swells. The addition of aqueous alcohol displaces the free triglyceride from the dispersion as a specifically light phase. The lecithins, in particular phosphatidylcholines, are soluble at low alcohol concentrations (see European patent document EP 1272048 B1 and the associated patent family).

In this alkaline solution-aqueous alcohol combination, the two or three phases
heavy=shells and 2) light=protein-lecithin-polyphenol-carbohydrate together with foam containing oil; or
heavy=shells, 2) medium=protein-lecithin-polyphenol-carbohydrate, 3) light=triglyceride, are advantageously separable, preferably centrifugally, in the experiment in the beaker or on the industrial scale.

The more successful the separation of the shells, the lower the protein losses and the greater the purity of the final product. Even the shell swollen as much as 7-fold by the addition of water is heavier than the proteins in the alcoholic-aqueous dispersion. This is essential for gravity separation. However, the separation is rendered more difficult by the protein-containing aleurone bodies (alveolar layer) adhering firmly to the shells. These cells are thick-walled. Because the cell membranes of nearly all cells contain lecithins (along with proteins and other substances), the adhesion can be minimized by using suitable measures to "solubilize" the lecithins.

Specifically, this is achieved by the fact that the aqueous phase has an alcohol concentration of 5-40 vol. % (see steps S2-S4), ideally 12% to 20%.

The decisive factor is the quality of the source material at the outset. The residual oil content is usually higher in cold-pressed cake. This does not interfere with the method presented here. In contrast: gentle pressing is extraordinarily helpful; the more moderate the press temperature and the lesser the press pressure, the easier it is to separate shells from cotyledons (seed leaves, the inside of the kernel) afterwards.

The method can also be used with "standard", i.e., hot-pressed press cake. The only thing is that the protein yields will be correspondingly lower.

Exemplary embodiments of the invention will now be described in connection with FIGS. 1 and 2, in which the supplying and the optional comminution according to steps A and B are not shown in detail for the sake of simplicity.

Following an addition of water, NaOH, and ethanol, which are preferably added separately but can also be added simultaneously, a separation into a heavy shell-containing phase and an upper section takes place. The additional advantageous extraction of recyclable materials from the upper section is described in FIG. 2 in particular.

In FIG. 1, diluted hydrochloric acid (HCl) is added to the heavy phase containing the shells (step F2-A). The processing took place at room temperature and at a pH of, say, 3.7.

The now dispersed phase is then separated into a shell fraction and into an upper section fraction in the manner already described in step F2-B.

The upper section fraction is then shifted into a less acidic pH range, preferably between 5.5 and 7, by adding an alkaline solution (e.g., NaOH or Ca(OH)$_2$ or KOH). The alkaline solution addition corresponds to step F2-61, depending upon whether just phytic acid as phytate is to be extracted or whether proteins are to be extracted from this fraction in addition.

Lastly, solids such as protein are separated from water and phytic acid in a manner analogous to steps H and F2-C. A second purification (separation of phytic acid and water) can be carried out in an optional step F2-D.

FIG. 2 shows the extraction of other recyclable products in addition to phytic acid. These extraction steps have already been described.

Although the present invention has been described above by means of embodiments with reference to the enclosed drawings, it is understood that various changes and developments can be implemented without leaving the scope of the present invention, as it is defined in the enclosed claims.

The invention claimed is:

1. A method for obtaining at least one or a plurality of recyclable materials from a native material quantity containing phytic acid or phytate, wherein the at least one recyclable material is phytic acid or at least one phytate, the method comprising:

Step A: supplying a native material quantity containing phytic acid or phytate from seeds containing phytic acid or phytate with hard, breakable shells as material quantity from the whole seeds or from seeds that have been at least partially de-oiled as expeller meal or as press cake left over as residue from oil extraction with a press;

Step B: if the material quantity from step A has not yet been comminuted, then comminuting the material quantity so that the shells are broken open;

Step C: dispersing the comminuted material quantity from step A) or B) with water or with an aqueous solution, wherein up to 8 parts maximum of water are added to one part of comminuted material quantity and wherein the water and the comminuted material quantity are stirred so as to give rise to a flowable mash or a dispersion;

Step D): adjusting a pH value of the mash from step C) in an alkaline range of pH >9.5;

Step E): adding a diluted water-soluble organic solvent to the mash D) subsequent to the adjustment of the pH of the mash in step D) in such a way that an alcohol concentration is reached that is less than 30% in order to detach the shells from the endosperm of the seeds/fruits;

Step F1): separating a solid phase, which has the predominant fraction of the shells, from the mash from step E), in a centrifuge in a centrifugal field; and Step F2): isolating phytic acid or of a phytate from the solid phase of step F1).

2. The method of claim 1, wherein step F2) comprises the sub-steps:

Step F2-A): mixing the solid phase from step F1) with water and/or with diluted hydrochloric acid so as to give rise to a flowable shell-containing and water-saturated phase containing phytic acid and/or phytate whose pH value is shifted into an acidic range; and Step F2-B): separating a solid phase, which has the predominant fraction of the shells, from a liquid phase containing phytic acid and/or phytate, and F2-C): separating the phytic acid from the liquid phase containing phytic acid or phytate directly or after carrying out one or a plurality of additional steps.

3. The method of claim 1, wherein the following sub-step is carried out between steps F2-B and F2-C:

F2-B1): shifting the pH value of the fluid phase from step F2-B) into a range with a pH value of pH>5.

4. The method of claim 1, further comprising:

Step G): shifting the pH value of the mash freed of shells from step F1) into the range of pH=4.5 to pH=7.2; and Step H): separating the shell-free mash whose pH value was shifted into the acidic range in step G) in at least one decanter or a separator into a plurality of phases, wherein one of these phases is a globulin-containing protein concentrate phase.

5. The method of claim 4, wherein in step H), the following phase separation is carried out in one or two steps in a decanter or separator:

oil-containing phase with triglyceride content;
   aqueous phase with albumin content; and
   the protein concentrate phase.

6. The method of claim 5, wherein in step H), the following phase separation into the following two recyclable material phases is carried out in one or two steps in a decanter or separator:

aqueous phase with albumin content and residual oil content; and
   the protein concentrate phase.

7. The method of claim 4, wherein the aqueous phase from step H) is filtered to build up the albumin concentration, in order to extract the albumin phase as a recyclable material.

8. The method of claim 4, wherein a protein concentrate phase is extracted that is assigned to the values RAL 1015 or RAL 1013 in a RAL color classification scale or is a mixture of these two color tones.

9. The method of claim 1, wherein an intermediate product produced before Step A is processed as the material quantity/source material no more than 31 days prior to Step A.

10. The method of claim 1, wherein the material quantity in step A is produced from a cold-pressed rape press cake, which was pressed at a temperature less than 70° C.

11. The method of claim 1, wherein one or a plurality of the separation steps of the preceding claims each take place in a 3-phase decanter or in at least two steps in 2-phase decanters.

* * * * *